United States Patent
Bausch et al.

(10) Patent No.: US 8,355,796 B1
(45) Date of Patent: Jan. 15, 2013

(54) SECONDARY SIDE LOAD DETECTION IN AN ELECTROTHERAPY APPARATUS

(75) Inventors: James F. Bausch, Salem, OR (US); George Vernon, Wancouver, WA (US); Aleksandr Gridasov, Vancouver, WA (US)

(73) Assignee: International Rehabilitative Sciences, Inc., Vancouver, WA (US)

( * ) Notice: Subject to any disclaimer, the term of this patent is extended or adjusted under 35 U.S.C. 154(b) by 1571 days.

(21) Appl. No.: 11/740,114

(22) Filed: Apr. 25, 2007

(51) Int. Cl.
*A61N 1/40* (2006.01)

(52) U.S. Cl. .................. 607/62; 607/8; 607/48; 607/63; 607/64

(58) Field of Classification Search .............. 607/8, 48, 607/62–64; 128/908
See application file for complete search history.

(56) References Cited

U.S. PATENT DOCUMENTS

| | | | |
|---|---|---|---|
| 3,656,065 A * | 4/1972 | Reinhard et al. | 330/10 |
| 4,706,674 A * | 11/1987 | Dieken et al. | 607/46 |
| 5,237,991 A * | 8/1993 | Baker et al. | 607/27 |
| 6,442,434 B1 * | 8/2002 | Zarinetchi et al. | 607/61 |
| 6,988,005 B2 | 1/2006 | McGraw et al. | |
| 7,005,914 B2 | 2/2006 | Balakrishnan et al. | |

* cited by examiner

*Primary Examiner* — Niketa Patel
*Assistant Examiner* — Hiba El-Kaissi
(74) *Attorney, Agent, or Firm* — Blank Rome LLP

(57) ABSTRACT

A load detecting circuit has a primary side and a secondary side with a secondary side patient load impedance input having a patient-side opto-isolator and a secondary side reference resistance load input having a reference-side opto-isolator coupled to the secondary side patient load impedance input. The circuit also includes at least one primary side output resistor, wherein the patient-side opto-isolator and the reference-side opto-isolator drive the at least one primary side output resistor and an integrator for operatively controlling the secondary side and conveying the patient load input and the reference load input to the primary side, where the patient load input and the reference load input are powered by a secondary side transformer winding.

6 Claims, 4 Drawing Sheets

SECONDARY SIDE LOAD DETECTION IN AN ELECTROTHERAPY APPARATUS

FIELD OF THE INVENTION

The present invention relates generally to electro-medical devices for delivering electrotherapy and more specifically, the present invention relates to electro-medical devices with load detection circuits.

DESCRIPTION OF RELATED ART

Electrotherapy has become an important component in the treatment of certain medical conditions. Such electro-medical treatments include neuro-electrical muscle stimulation (NEMS), transcutaneous electrical nerve stimulation (TENS), microcurrent, sequential stimulation, etc. They have been used in the treatment of pain, to promote bone fusion, and to rehabilitate muscles following injury or surgery.

During electrotherapy, when a surface electrode loses contact with the skin of the patient, there is a risk of different abnormal situations, for example, a point contact from the electrode to the patient. Point contact results in high current density, causing an electric shock effect to the patient. When the electro-medical device is in a high frequency mode, this open circuit is easy to detect but it becomes more difficult to detect in lower frequency modes, i.e., muscle stimulation modes. A worst case scenario is the patient adjusting intensity without sensory feedback (electrode disconnected), in which case the intensity can cause severe spasms upon reconnection. If electrotherapy equipment produces such shocks, the patient is more prone to discontinue use and not avail themselves of the benefits of the treatment.

Load detection as a measurement of the primary current has merit in that the circuitry is simplified, since there is no need to convey information over an electrically isolated barrier. However, for extended pulses and even for light loads, there is still a significant component of measured current due to that required to magnetize the transformer core. That nuisance current creates an error term in the detection circuitry.

Prior art systems have used different methods for load detection. A load detect circuit, disclosed in U.S. Pat. No. 6,988,005, includes an output voltage signal which is measured across a known load resistance. That signal is amplified and fed back into the analog-to-digital conversion system contained within the processor for the system. That provides a measurement of the actual load experienced across the output of the transformer contained in each of the four drive circuits such that both open circuit (that is, no load conditions) and short circuit conditions can be detected. However, the load detection circuit does not perform as well as needed at low frequency range, muscle stimulation modes and does not account for nuisance current for extended pulses and light loads.

Thus, there is a need in the prior art for a load detection system that performs well at low frequencies and can account for nuisance currents to prevent a shocking effect being introduced to the patient.

SUMMARY OF THE INVENTION

It is therefore an object of the invention to provide circuits and processes for detecting loads by electro-medical devices for delivering electrotherapy.

To achieve the above and other objects, the present invention is directed to detect a patient/user load presence on the secondary side of the transformer then convey that load information to the control circuitry on the primary side. The present invention overcomes the disadvantages of the prior art systems discussed above.

According to at least one embodiment, the invention is directed to a load detecting circuit having a primary side and a secondary side, having a secondary side patient load impedance input having a patient-side opto-isolator and a secondary side reference resistance load input having a reference-side opto-isolator coupled to the secondary side patient load impedance input.

The device also includes at least one primary side output resistor, wherein the patient-side opto-isolator and the reference-side opto-isolator drive both primary side output resistors and an integrator for operatively controlling the secondary side and conveying the patient load input and the reference load input to the primary side, where the patient load input and the reference load input are powered by a secondary side transformer winding.

In addition, the load detecting circuit may include a first grounded base amplifier coupled between the patient-side opto-isolator and the integrator and a second grounded base amplifier coupled between the reference-side opto-isolator and the integrator. The integrator may be connected to the at least one primary side output resistor. The integrator may accumulate a difference in the reference load input and the patient load input, with the logic level indicating whether the patient load input is not equivalent to the reference load input. The patient-side opto-isolator and the reference-side opto-isolator can provide electrical isolation from the patient load input to the primary side. The integrator may also be provided through analog to digital converters and a processor adapted to integrate analog-to-digital converted signals.

According to at least another embodiment, an electro-medical device includes at least one pair of electrodes, a primary transformer winding and a load detecting circuit according to that described above. The secondary side patient load impedance input may be coupled to one of the at least one pair of electrodes. Also, the load detecting circuit provides electrical isolation from the patient load input to the primary side.

The present invention is also directed to a load detecting circuit having a primary side and a secondary side, with a secondary side patient load impedance input and a secondary side reference resistance load input coupled to the secondary side patient load impedance input through a coupler. The circuit also includes at least one primary side output resistor, wherein the coupler drives the at least one primary side output resistor and an integrator conveying the patient load impedance input and the reference resistance load input to the primary side. The coupler includes at least two, separate opto-isolators and the patient load impedance input and the reference load input are powered by a secondary transformer winding.

The load detecting circuit may include a first grounded base amplifier coupled between one of the opto-isolators and the integrator and a second grounded base amplifier coupled between another of the opto-isolators and the integrator. The integrator may be provided by a rail-to-rail integrator having a logic output indicating a presence of a patient load. In addition, the patient-side opto-isolator and the reference-side opto-isolator can provide electrical isolation between the patient load input and the primary side. The integrator can be provided by analog to digital converters and a processor adapted to integrate analog to digital converted signals. The processor may output a signal to a drive stage to remove a drive to a transformer winding when a lack of a patient load is detected. A simple integrating means can be an RC operational amplifier.

BRIEF DESCRIPTION OF THE DRAWINGS

A preferred embodiment of the present invention will be set forth in detail with reference to the drawings, in which.

DETAILED DESCRIPTION OF THE INVENTION

Figure 1:
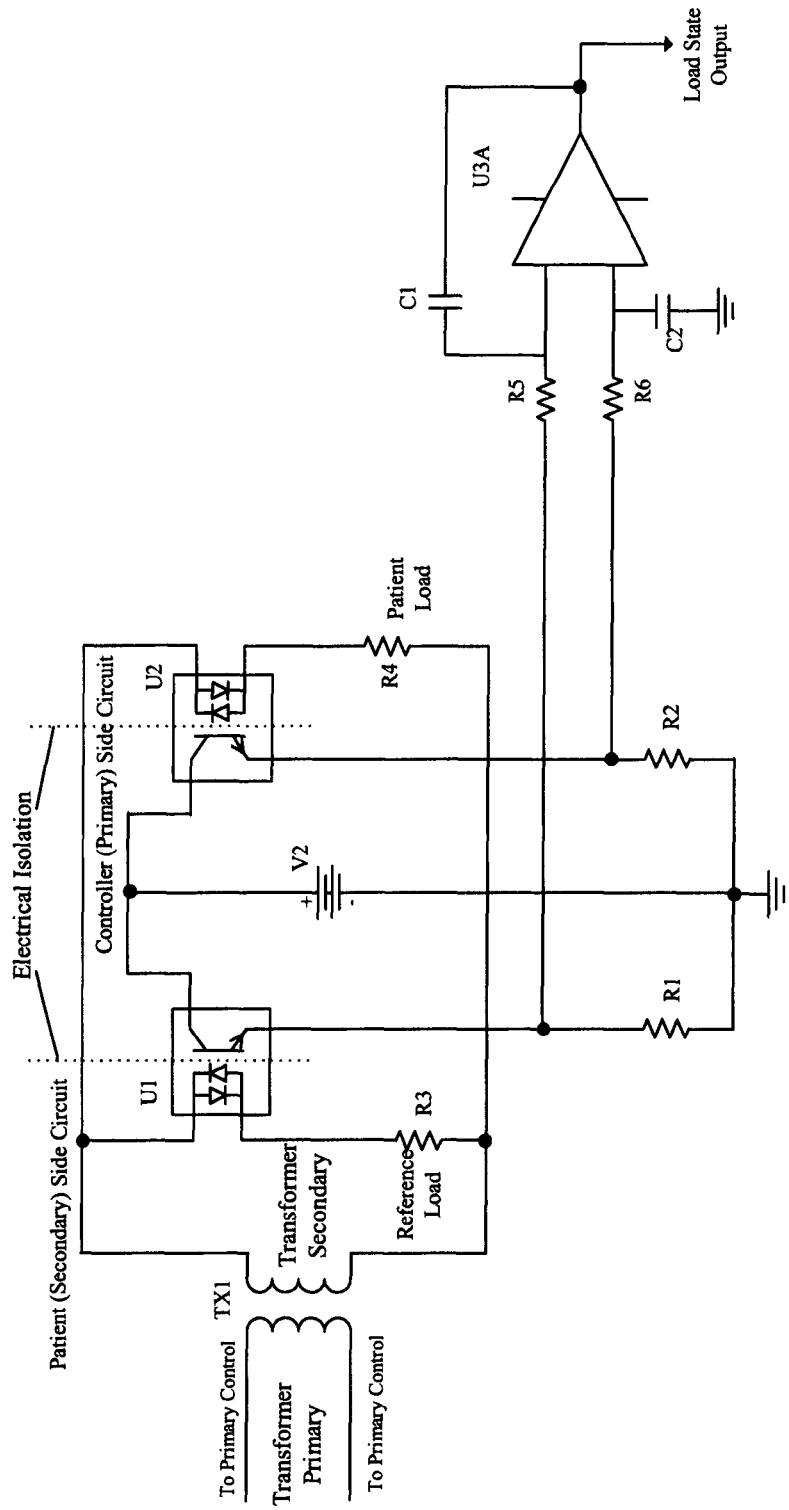
FIG. 1 shows a schematic rendering of a load detection circuit, according to one embodiment of the present invention.

The present invention will be set forth in detail with reference to the drawings, in which like reference numerals refer to like elements or operational steps throughout.

The present invention is directed to circuits and processes for detecting open circuits in both low and higher frequency modes. The present invention detects patient load presence on the secondary side of a transformer and conveys that information to control circuitry on the primary side.

Referring to FIG. 1, the transformer TX1 provides the voltage boost for patient muscle stimulation. The patient's body, represented by resistor R4, is connected through a bi-directional Light Emitting Diode (LED) on U2, which acts as an opto-isolator. A dummy reference resistor, R3, is connected to a similar opto-isolator U1.

With further reference to FIG. 1, if the patient load R4 is identical to reference resistor R3 during operation, pulses into LED's at U1 and U2 will provide identical pulses on R1 and R2. A bridge circuit is formed with each opto-isolator and the two ground-referenced output resistors R1 and R2. Any difference in resistance between the reference and patient loads will create an amplitude difference in the two output pulses on R1 and R2. Since the pulses can be very narrow, an integrator U3A is used to average out the pulse height differences over time.

Figure 2:
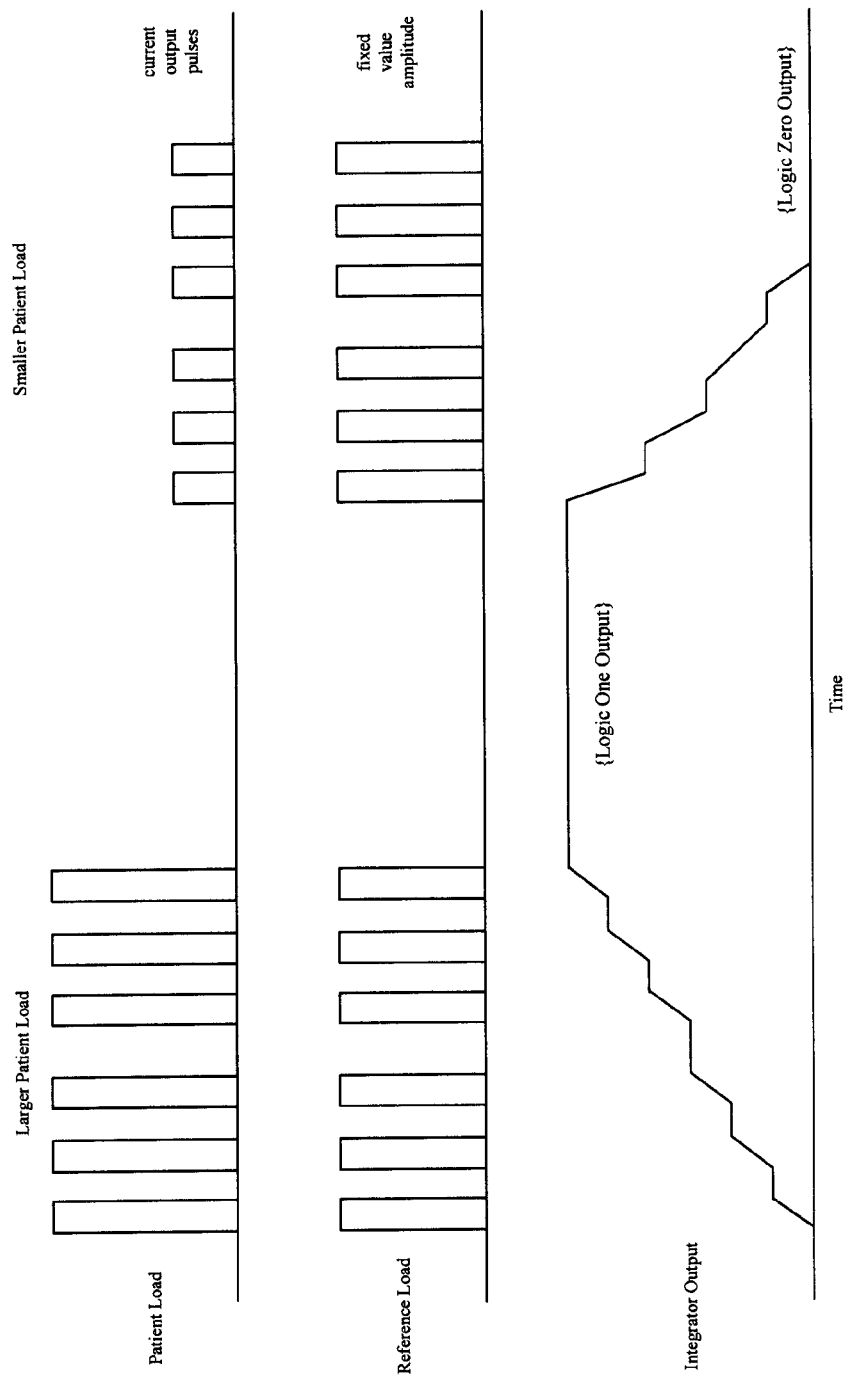
FIG. 2 is a graph which shows integrator output in response to changes in patient load when compared to the reference load, according to one aspect of the present invention.

The pulse area difference drives the integrator to the positive or negative rail, depending on the patient impedance being smaller or larger than the reference load. The rise time of the integrator output is proportional to the difference between patient and reference loads. FIG. 2 shows the effect of the pulse difference on the integrator.

One advantage in using the integrator is that there can be no long-term error in its output. For a steady stream of pulses arising from a constant patient load, the integrator must settle to either one rail or the other. The concept is similar to a type one servo system that has a single integrator in the forward path of the control loop. In servo systems, the single integrator assures that there is no final value (steady state) position error. The use of a single integrator assures no final value ambiguity in sensing the bridge difference.

The rail-to-rail integrator has a logic output that can be used for a logic level to a processor that is a part of the medical device. Logic 'ONE' indicates the presence of a patient load, i.e. a load resistor less than the 20 k-ohm reference resistor.

The integrator's output can be read via a processor's input/output pins. If the processor detects a zero, it has the task of removing the drive to the transformer primary. The transformer drive will remain removed until the patient/operator/user has had the opportunity to reconnect his conductive patch and restart the stimulator.

Some types of muscle stimulators have pulses that are extremely short in duration, such that a conventional opto-isolator may not be able to respond to the pulse. The addition of a grounded base amplifier (shown in FIG. 3) can be incorporated between each opto-isolator and the integrator to accommodate faster pulse rates. The two transistors Q1 and Q3 have their emitters connected to the opto-isolators U4 and U5 and their bases connected to power source V3.

Frequency limitations in opto-isolators arise from the parasitic capacitance from the collector to the base in the device's phototransistor. Even though very small in magnitude, this capacitor can inject excessive current into the base of the phototransistor during switching, which slows the rise time of the collector. From another perspective, a small photon induced current cannot charge the small base/collector capacitance to a very high voltage in the required time period. That apparent increase in base collector capacitance is called the Miller Effect.

Figure 3:
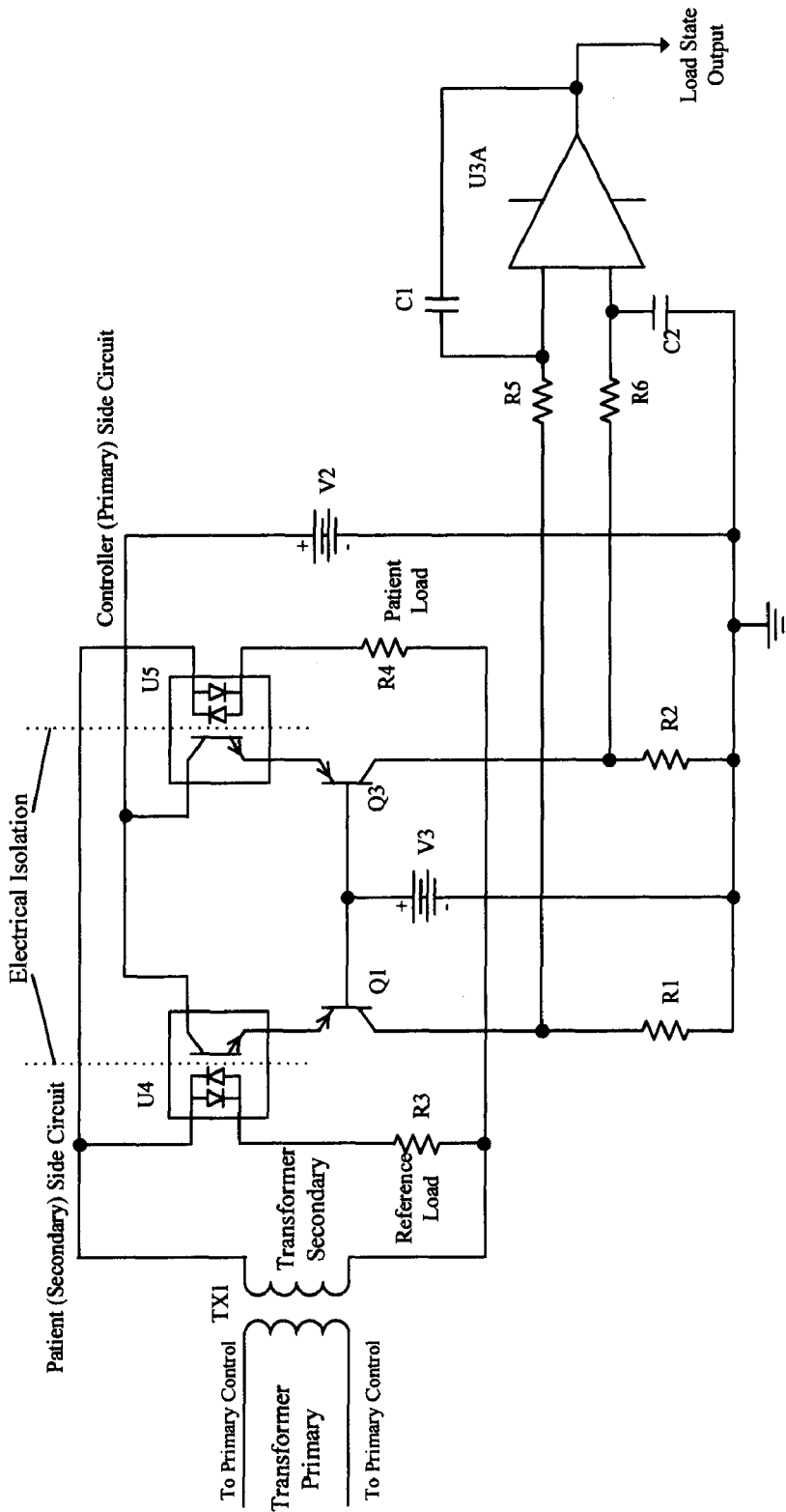
FIG. 3 shows a schematic rendering of a load detection circuit, with a grounded base amplifier, according to another embodiment of the present invention.

Still referring to FIG. 3, with the addition of the grounded base amplifier, the charge required to affect a voltage change at the opto-isolator's collector is minimal, since the collectors are effectively AC grounded and their emitters are tied to the emitters of Q1 and Q2. The required opto-isolator output voltage swings are minimal due to the lower input impedance of the grounded emitter amplifiers. The photo-induced currents of the opto-isolators pass through the emitters of Q1 and Q2. The very low impedances on the bases of Q1 and Q2 can supply charge to the small capacitance from their collectors. The final result is a speed-enhanced opto-isolator that is no longer subject to the limitations of Miller Effect capacitance. Whereas the circuit in FIG. 1 has no frequency limitations with pulses less than 1 kHz repetition rates, the grounded base amplifier allows operation in excess of 50 kHz.

Figure 4:
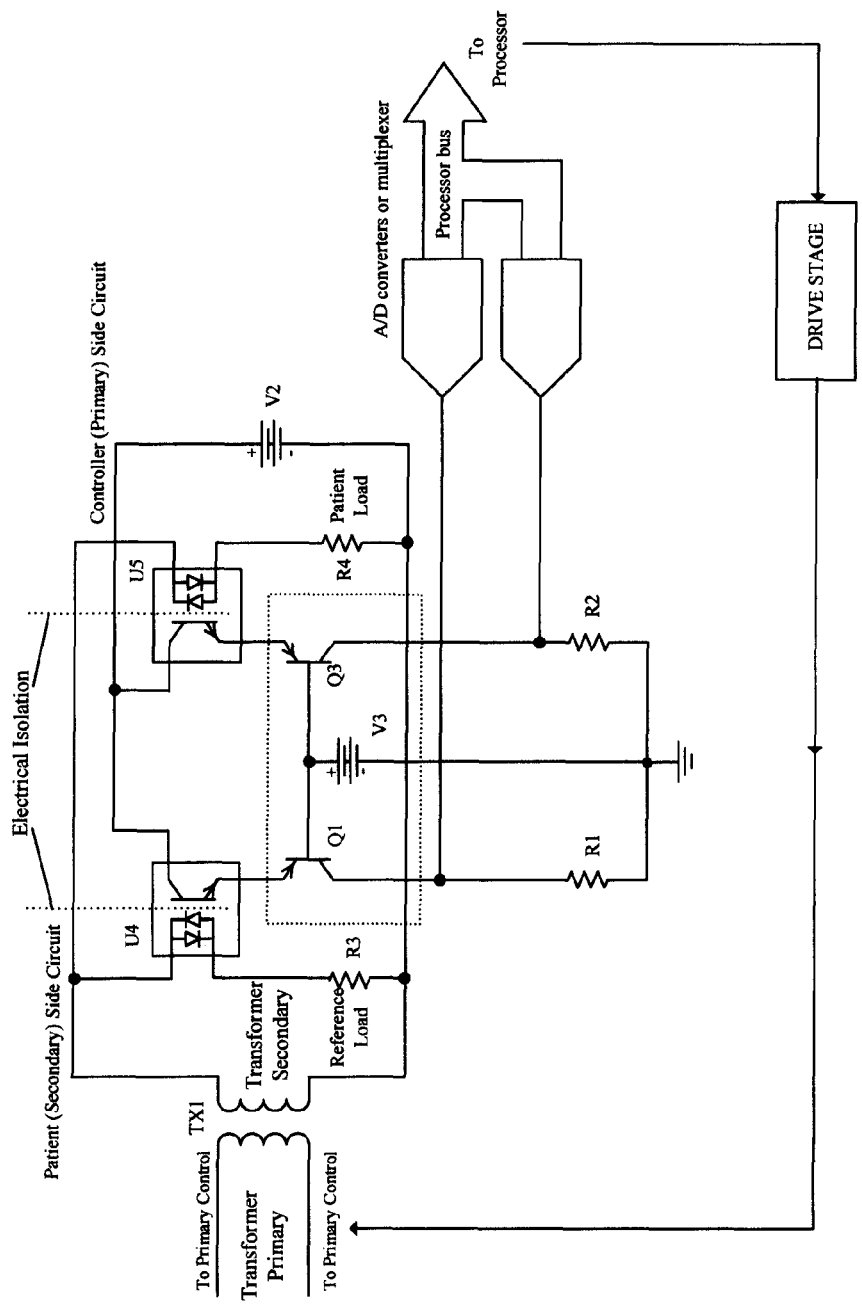
FIG. 4 shows a schematic rendering of a load detection circuit using a processor in place of the integrator found in FIG. 3, according to another embodiment of the present invention.

Referring now to FIG. 4, in another embodiment an imbedded processor may replace the integration function. FIG. 4 shows a configuration that employs analog-to-digital converters and a processor to replace the integrator. The processor actively monitors the difference in pulse height and accumulates the result. This technique is especially economical if the analog-to-digital converter and multiplexer are both within the processor.

A method for detecting a load using a load detecting circuit will now be discussed. Pulses are detected in both patient-side and reference-side opto-isolators to produce a primary and a secondary signal, respectively. A difference between the primary and secondary signals is determined through a bridge circuit to produce an amplitude difference in an output pulse. The series of output pulses is integrated through an integrator to produce an average pulse height over time and thereby driving the integrator to a positive rail or a negative rail based on the average pulse height. The circuit then outputs a logical signal indicating a presence of a patient load based on whether the integrator is driven to the positive or negative rails. A processor detects the logical signal and removes a driving signal from a transformer primary when the logical signal so dictates. As discussed above, the integrating, driving and outputting steps can be substituted by the conversion of the output pulse signals to digital signals through analog to digital converters and integrating the analog to digital converted signals to produce the logical signal. This later process makes use of the processor for the integrating function and does not rely on a separate circuit portion.

The present invention can be used in devices that have high frequency modes, such as interferential and muscle stimulation devices. Primary side detection can cause primary currents to pollute the patient current with artifact currents such as magnetization currents, inter-winding capacitance charging currents, and saturation currents due to wide pulses. The present invention is a safety circuit that turns off the current and improves the process of load detection when compared to the prior art processes.

While a preferred embodiment of the invention has been set forth above, those skilled in the art who have reviewed the present disclosure will readily appreciate that other embodiments can be realized within the scope of the invention. For example, numerical values are illustrative rather than limiting, as are specific techniques for attenuation and the like. Therefore, the present invention should be construed as limited only by the appended claims.

What is claimed is:

1. A load detecting circuit having a primary side and a secondary side, comprising:
   a secondary side patient load impedance input;
   a secondary side reference resistance load input coupled to said secondary side patient load impedance input through coupling means;
   at least one primary side output resistor, wherein the coupling means are configured to drive the at least one primary side output resistor; and
   an integrating means configured to convey the patient load impedance input and the reference resistance load input to the primary side;
   wherein the coupling means comprise at least two, separate opto-isolators and the patient load impedance input and the reference load input are powered by a secondary side transformer winding.

2. The load detecting circuit of claim 1, further comprising:
   a first grounded base amplifier coupled between one of the opto-isolators and said integrating means; and,
   a second grounded base amplifier coupled between another of the opto-isolators and said integrating means.

3. The load detecting circuit of claim 1, wherein the integrating means comprise a rail-to-rail integrator having a logic output configured to indicate a presence of a patient load.

4. The load detecting circuit of claim 1, wherein the two, separate opto-isolators comprise a patient-side opto-isolator and a reference-side opto-isolator, and wherein the patient-side opto-isolator and the reference-side opto-isolator provide electrical isolation from said patient load input to the primary side.

5. The load detecting circuit of claim 1, wherein the integrating means comprises analog to digital converters and a processor adapted to integrate analog to digital converted signals.

6. The load detecting circuit of claim 1, wherein the processor outputs a signal to a drive stage to remove a drive to a primary side transformer winding when a lack of a patient load is detected.

* * * * *